United States Patent [19]

Murtha

[11] 4,115,207
[45] Sep. 19, 1978

[54] SEPARATION OF PHENOL-, CYCLOHEXANONE-, AND CYCLOHEXYLBENZENE-CONTAINING MIXTURES EMPLOYING A TRISUBSTITUTED PHOSPHATE

[75] Inventor: Timothy P. Murtha, Bartlesville, Okla.

[73] Assignee: Phillips Petroleum Company, Bartlesville, Okla.

[21] Appl. No.: 819,422

[22] Filed: Jul. 27, 1977

[51] Int. Cl.$^2$ .................. B01D 3/40; C07C 39/04; C07C 45/24
[52] U.S. Cl. ....................... 203/60; 203/84; 260/586 R; 568/757
[58] Field of Search ............ 203/38, 57, 51, 84, 203/60; 260/586 P, 586 R, 621 A, 621 C

[56] References Cited

U.S. PATENT DOCUMENTS

| | | | |
|---|---|---|---|
| 2,171,795 | 9/1939 | Kautter | 203/60 |
| 2,762,760 | 9/1956 | Walker | 260/621 A |
| 4,016,049 | 4/1977 | Fozzard et al. | 260/621 A |
| 4,019,965 | 4/1977 | Fozzard | 260/621 C |
| 4,021,490 | 5/1977 | Hudson | 260/621 C |

Primary Examiner—Wilbur L. Bascomb, Jr.

[57] ABSTRACT

Phenol-, cyclohexanone-, and cyclohexylbenzene-containing mixtures are extractively distilled to provide overhead of cyclohexanone and a kettle product containing phenol and, when present, cyclohexylbenzene by employing a trisubstituted phosphate agent or solvent.

4 Claims, 1 Drawing Figure

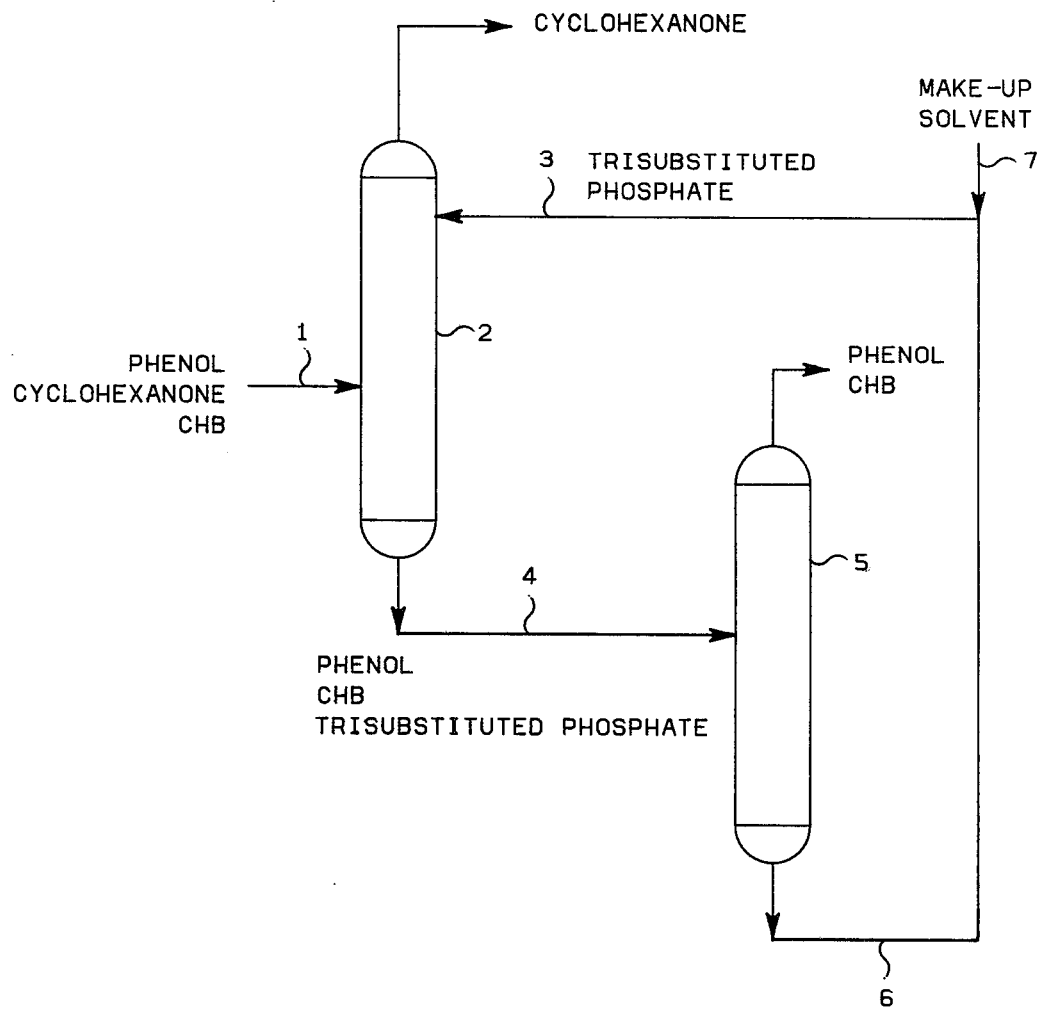

SEPARATION OF PHENOL-, CYCLOHEXANONE-, AND CYCLOHEXYLBENZENE-CONTAINING MIXTURES EMPLOYING A TRISUBSTITUTED PHOSPHATE

This invention relates to the separation of phenol from its azeotropes, including phenol-cyclohexanone azeotrope, which may be in presence of cyclohexylbenzene. In one of its aspects, the invention relates to recovery of phenol and cyclohexanone from the cleavage products resulting from cleavage of the oxidation product of cyclohexylbenzene to provide cyclohexylbenzene hydroperoxide which then is converted to produce the phenol, cyclohexanone, and any unreacted cyclohexylbenzene.

In one of its concepts, the invention provides a process for extractive distillation of a mixture containing phenol and cyclohexanone employing as an agent a trisubstituted phosphate. In another of its concepts, the invention provides such a process in which cyclohexanone is obtained as a high purity overhead while the solvent, i.e., trisubstituted phosphate, containing the phenol and to the extent present cyclohexylbenzene is removed as bottoms. In a further concept of the invention, the bottoms are fractionated or extractively distilled to obtain phenol and cyclohexylbenzene as an overhead, the trisubstituted phosphate solvent as bottoms, and the bottoms are again used in the initial extractive distillation.

Cyclohexhlbenzene (CHB) can be converted to phenol and cyclohexanone via cyclohexylbenzene hydroperoxide. The acid catalyzed cleavage of cyclohexylbenzene hydroperoxide in the presence of unoxidized CHB results in a mixture of CHB, phenol, and cyclohexanone. This mixture is difficult to separate by conventional distillation techniques because phenol and cyclohexanone form an azeotrope (b.p. 184° C at atmospheric pressure) containing about 72 weight percent phenol. In addition, CHB codistills with this azeotrope.

It is an object of this invention to separate mixtures containing phenol and cyclohexanone which also can contain cyclohexylbenzene. It is another object of this invention to provide an extractive distillation agent or solvent to separate mixtures as described herein. It is a still further object of the invention to provide an extractive distillation operation comprising a mixture of one or more agents or solvents also as described herein.

Other aspects, concepts, objects, and the several advantages of the invention are apparent from a study of this disclosure, the drawing, and the appended claims.

According to the present invention, a mixture containing phenol and cyclohexanone, which may contain cyclohexylbenzene, is extractively distilled employing a trisubstituted phosphate and thus separated to produce as an overhead product a fraction containing essentially cyclohexanone and as bottoms a mixture containing the solvent, phenol, and cyclohexylbenzene which may have been present.

Mixture to be Separated

In the practice of the process of this invention, any mixture of phenol, cyclohexanone, and CHB or mixture of phenol and cyclohexanone can be used. It is within the scope of this invention to remove by suitable methods a portion of any of the components from the mixture to be separated before the extractive distillation with the trisubstituted phosphates. For example, any excess of cyclohexanone over the quantity present in the azeotrope can be first distilled from the mixture as an essentially pure material. Since CHB codistills with the phenol/cyclohexanone azeotrope in quantities of about 2 to 10 weight percent, any excess of CHB over that amount can be separated by fractional distillation in taking the phenol/cyclohexanone mixture containing about 2 to 10 weight percent CHB overhead.

It is also within the scope of this invention to remove essentially all of the CHB from the mixture by suitable techniques, such as extractive distillation, before the extractive distillation of this invention.

Solvent

The trisubstituted phosphate solvent which can be used in the extractive distillation of this invention can contain up to 30 carbon atoms and can be represented by the following general formula: $(RO)_3PO$ wherein each R is selected from a group consisting of alkyl radicals containing 4 to 18 carbon atoms, cycloalkyl radicals containing 5 to 12 carbon atoms, aryl or substituted aryl radicals containing 6 to 12 carbon atoms with the substituent groups being one or more or a mixture of alkyl, cycloalkyl, alkoxy, halogen, or the like, and aralkyl radicals containing 7 to 12 carbon atoms, the solvent having a boiling point above the boiling point of phenol (182° C at atmospheric pressure) to facilitate the separation of the solvent for recycling by fractional distillation. However, low levels of phenol (up to about 10 weight percent phenol) can be present in the recovered and recycled solvent with no detrimental effect on the extractive distillation. For ease of handling, it is generally preferred that it be a liquid or low melting (below about 80° C) solid.

Specific examples of trisubstituted phosphates that are suitable for the extractive distillation of this invention include tributyl phosphate, trihexyl phosphate, tricyclohexyl phosphate, tribenzyl phosphate, triphenyl phosphate, tritolyl phosphate (tricresyl phosphate), tri-p-chlorophenyl phosphate, diphenyl cresyl phosphate, and the like. These compounds are either commercially available or can be prepared by known methods. For example, the reaction of phenol with phosphorus oxychloride ($POCl_3$) yields triphenyl phosphate.

The currently preferred solvent for the extractive distillation of this invention is triphenyl phosphate.

Extractive Distillation Conditions

The extractive distillation of this invention can be carried out under a variety of conditions. The volume ratio of trisubstituted phosphate to feedstream will be broadly from 0.1/1 to 10/1, preferably 1/1 to 5/1. To avoid possible thermal decomposition or other reactions during the extractive distillation, head temperatures below 135° C, preferably below 100° C, are used with a reduced pressure sufficient to allow the separation to occur.

Referring to the diagram, a feed mixture consisting essentially of phenol, cyclohexanone, and CHB is passed by 1 to an extractive distillation column 2. The trisubstituted phosphate solvent of this invention is introduced into the extractive distillation column 2 by 3 at a point above the point of introduction of the feed mixture.

A vaporous overhead stream consisting essentially of cyclohexanone is withdrawn from the extractive distillation column 2. A liquid bottoms stream consisting essentially of phenol, CHB, and trisubstituted phosphate is withdrawn from the extractive distillation column 2 by 4 and passed to a distillation column 5.

In the distillation column 5, the phenol-CHB-trisubstituted phosphate mixture is separated into a vaporous overhead stream consisting essentially of phenol and CHB and a liquid bottoms stream consisting essentially of trisubstituted phosphate which is passed by 6 and 3 to the extractive distillation column 2. Makeup trisubstituted phosphate is added by 7 if necessary. The phenol-CHB overhead stream can be passed to another separation stage to separate this mixture.

When the mixture to be separated consists essentially of phenol and cyclohexanone, e.g., when CHB has been first removed from a phenol-cyclohexanone-CHB mixture, the bottom stream from extractive distillation column 2 will consist essentially of phenol and trisubstituted phosphate and the overhead stream from distillation column 5 will consist essentially of phenol.

EXAMPLES

In the following examples, extractive distillations were conducted in an electrically heated 0.75" (19 mm) diameter × 36" (914 mm) length column containing 0.25" (6.4 mm) Por-Pak stainless steel perforated screen packing. The solvent was fed through a rotameter and heating section to an introduction port 3" (76 mm) from the top of the column. The mixture to be separated was fed through a rotameter and heating section to an introduction port 18" (457 mm) from the top of the column. The overhead and kettle products were collected and then analyzed by gas-liquid phase chromatography (glpc) on a Hewlett Packard 5710A chromatograph equipped with a flame ionization detector.

Fractional distillations were conducted with an electrically heated 0.75" (19 mm) diameter × 24" (610 mm) or 8" (203 mm) length column containing #3008 stainless steel Heli-Pak [0.092" (2.34 mm) × 0.175" (4.44 mm) × 0.175" (4.44 ml)] packing. The overhead products were collected and then analyzed by glpc.

The mixtures to be separated were prepared from commercial, reagent grade phenol and cyclohexanone and cyclohexylbenzene (98% purity) prepared by the reductive alkylation of benzene. Extractive distillation solvents were commercial materials. Tritolyl phosphate contains a mixture of o, m, and p isomers.

EXAMPLE I

Two runs (Runs 1 and 2) were conducted according to the instant invention utilizing triphenyl phosphate as the solvent for the extractive distillation of a mixture containing 68 weight percent phenol, 27 weight percent cyclohexanone, and 5 weight percent CHB.

The extractive distillation conditions in Run 1 were 120 mm Hg pressure, 85°–88° C head temperature, and 1.58/1 solvent/feed volume ratio. Over a 4.5-hour run time, the overhead fractions contained cyclohexanone with an average purity of 98.4 weight percent. The cyclohexanone collected was 64.5 weight percent of the amount of cyclohexanone fed to the column during the run.

Run 2 was conducted in a manner similar to Run 1 except the pressure was 118 mm Hg pressure, the head temperature was 88°–90° C, and the solvent/feed volume ratio was increased to 2.4/1. Over a 5.75-hour run time, the overhead fractions contained cyclohexanone with an average purity of 98.7 weight percent. The cyclohexanone collected was 92.4 weight percent of the amount of cyclohexanone fed to the column during the run.

The kettle product from Run 2 was fractionally distilled at 65 mm Hg pressure to cleanly separate phenol and CHB in overhead fractions from the triphenyl phosphate solvent.

The results of these runs demonstrate operability of this invention utilizing triphenyl phosphate as solvent for the separation of cyclohexanone in high yield and high purity from a mixture of cyclohexanone, phenol, and CHB and for the recovery of triphenyl phosphate solvent for recycle.

EXAMPLE II

Run 3 was conducted according to the instant invention utilizing tritolyl phosphate as the solvent for the extractive distillation of a mixture containing 68 weight percent phenol, 27 weight percent cyclohexanone, and 5 weight percent CHB. The extractive distillation conditions were 120 mm Hg pressure, 85°–92° C head temperature, and 1.95/1 solvent/feed volume ratio. Over a 2.5-hour run time, the overhead fractions contained cyclohexanone with an average purity of 99.2 weight percent. The cyclohexanone collected was 64.2 weight percent of the amount of cyclohexanone fed to the column during the run.

The results of this run show that tritolyl phosphate separates cyclohexanone in high purity from a mixture of phenol, cyclohexanone, and CHB. As shown in Example III, a higher solvent/feed ratio allows a larger amount of the cyclohexanone to be collected.

EXAMPLE III

Two runs (Runs 4 and 5) were conducted according to the instant invention utilizing tritolyl phosphate as the extractive distillation solvent for the extractive distillation of a mixture containing 68 weight percent phenol, 27 weight percent cyclohexanone, and 5 weight percent CHB.

The extractive distillation conditions in Run 4 were 120 mm Hg pressure, 88°–89° C head temperature, and 2.6/1 solvent/feed volume ratio. Over a 2-hour run time, the overhead fractions contained cyclohexanone with an average purity of 98.4 weight percent. The cyclohexanone collected was 95.2 weight percent of the amount of cyclohexanone fed to the column during the run.

The kettle product from Run 4 was fractionally distilled at 120 and 65 mm Hg pressure to separate overhead fractions containing predominantly phenol and CHB from the tritolyl phosphate solvent.

Run 5 was conducted in a manner similar to Run 4 except the head temperature was 87° C. Over a 2.5-hour run time, the overhead fractions contained cyclohexanone with an average purity of 98.1 weight percent. The cyclohexanone collected was 100 weight percent of the amount of cyclohexanone fed to the column during the run. Following this run, extractive distillation conditions were changed to 65 mm Hg pressure in an attempt to bring CHB overhead. Although a variety of conditions (temperatures and solvent/feed volume ratios) were tried, the overhead product contained predominantly cyclohexanone and phenol.

The results of these runs demonstrate operability of this invention utilizing tritolyl phosphate as solvent for the separation of cyclohexanone from a mixture of cyclohexanone, phenol, and CHB and for the recovery of tritolyl phosphate solvent for recycle.

EXAMPLE IV

Two runs (Runs 6 and 7) were conducted according to the instant invention utilizing tritolyl phosphate as solvent for the extractive distillation of mixtures of phenol and cyclohexanone.

The extractive distillation of Run 6 used a feed mixture containing 70 weight percent phenol and 30 weight percent cyclohexanone and the conditions were 100 mm Hg pressure, 64°–67° C head temperature, and 2.7/1 solvent/feed volume ratio. Over a 4-hour run time, the overhead fractions contained 85.7 weight percent of the cyclohexanone fed to the column with a purity of 99.3 weight percent.

The extractive distillation of Run 7 used a feed mixture containing 50 weight percent phenol and 50 weight percent cyclohexanone and the conditions were 50 mm Hg pressure, 59°–61° C head temperature, and 2.7/1 solvent/feed volume ratio. Over a 6-hour run time, the overhead fractions contained 97.8 weight percent of the cyclohexanone fed to the column with a purity of 99.6 weight percent.

The results of these runs demonstrate operability of this invention utilizing tritolyl phosphate as solvent for the separation of cyclohexanone in high yield and high purity from a mixture of phenol and cyclohexanone.

EXAMPLE V

Two runs (Runs 8 and 9) were conducted to evaluate the effect of added n-butanol and γ-butyrolactone in the feed mixture on the overhead stream composition during an extractive distillation with tritolyl phosphate as solvent.

Run 8 was conducted with a feed mixture containing 65 weight percent phenol, 25 weight percent cyclohexanone, 5 weight percent CHB, and 5 weight percent n-butanol. The extractive distillation conditions were 65 mm Hg pressure, 103°–107° C head temperature, and 5.7/1 solvent/feed volume ratio. Over the 1.5-hour run time, the overhead fractions contained predominantly n-butanol, cyclohexanone, and phenol.

Run 9 was conducted with a feed mixture containing 65 weight percent phenol, 25 weight percent cyclohexanone, 5 weight percent CHB, and 5 weight percent γ-butyrolactone. The extractive distillation conditions were 65 mm Hg pressure, 70° C head temperature, and 4.1/1 solvent/feed volume ratio. Over a 1-hour run time, the overhead fraction contained 100 weight percent of the cyclohexanone fed to the column during the run with a purity of 96.8 weight percent.

The results of these runs indicate that the presence of n-butanol in the feed mixture is detrimental to the extractive distillation of this invention and that the presence of γ-butyrolactone in the feed mixture does not significantly change the results of the extractive distillation of this invention.

EXAMPLE VI

In a control run, an extractive distillation of a mixture containing 68 weight percent phenol, 27 weight percent cyclohexanone, and 5 weight percent CHB was conducted with phenyl salicylate as solvent. The conditions were 80 mm Hg pressure, 85°–93° C head temperature, and a solvent/feed ratio of 3.06/1. Over a three-hour run time, the overhead product contained 58.3 weight percent of the cyclohexanone fed to the column with a purity of 33.9 weight percent.

This extractive distillation was repeated with the same solvent, but with the pressure increased to 100 mm Hg, the head temperature increased to 99°–102° C, and the solvent/feed ratio increased to 3.2/1. Over a 4-hour run time, the overhead product contained 90.6 weight percent of the cyclohexanone fed to the column with a purity of 25.9 weight percent.

Thus, phenyl salicylate, a solvent outside the scope of this invention, does not cleanly separate cyclohexanone from the mixture of cyclohexanone, phenol, and CHB.

EXAMPLE VII

In another control run, an extractive distillation of a mixture containing 70 weight percent phenol and 30 weight percent cyclohexanone was conducted with methyl oleate as solvent. The conditions were 100 mm Hg pressure, 53°–73° C head temperature, and a solvent/feed volume ratio of 4.2/1. Over a 7-hour run time, the overhead fractions contained 48.1 weight percent of the cyclohexanone fed to the column with a purity of 94.7 weight percent.

Thus, methyl oleate, a solvent outside the scope of this invention, does not cleanly remove cyclohexanone from a mixture of phenol and cyclohexanone.

Reasonable variation and modification are possible within the scope of the foregoing disclosure, drawing, and appended claims to the invention the essence of which is that a trisubstituted phosphate solvent boiling above phenol has been found highly effective to separate a phenol-cyclohexanone azeotrope.

I claim:

1. An extractive distillation of a mixture containing phenol and cyclohexanone, which mixture may contain cyclohexylbenzene, which comprises distilling said mixture in the presence of a solvent comprising a trisubstituted phosphate boiling above phenol and containing up to 30 carbon atoms.

2. A process according to claim 1 wherein the solvent which is used in the extractive distillation of this invention contains up to 30 carbon atoms and is represented by the following general formula: $(RO)_3PO$, wherein each R is selected from a group consisting of alkyl radicals containing 4 to 18 carbon atoms, cycloalkyl radicals containing 5 to 12 carbon atoms, aryl or substituted aryl radicals containing 6 to 12 carbon atoms with the substituent groups being one or more or a mixture of alkyl, cycloalkyl, alkoxy, halogen, or the like, and aralkyl radicals containing 7 to 12 carbon atoms, the solvent having a boiling point above the boiling point of phenol (182° C at atmospheric pressure) to facilitate the separation of the solvent for recycling by fractional distillation.

3. An extractive distillation of a mixture containing phenol and cyclohexanone, which mixture may contain cyclohexylbenzene, which comprises employing as a solvent, a trisubstituted phosphate selected from the following: tributyl phosphate, trihexyl phosphate, tricyclohexyl phosphate, tricyclohexyl phosphate, triphenyl phosphate, tritolyl phosphate (tricresyl phosphate), tri-p-chlorophenyl phosphate, and diphenyl cresyl phosphate.

4. An extractive distillation of a mixture containing phenol and cyclohexanone, which mixture may contain cyclohexylbenzene, which comprises employing as a solvent, a trisubstituted phosphate boiling above phenol and containing up to 30 carbon atoms in the molecule and wherein there is recovered as an overhead product cyclohexanone and as bottoms a solvent containing phenol and any cyclohexylbenzene which has been present, the bottoms or fractionator recover the solvent which can be reused.

* * * * *